United States Patent [19]

Krause et al.

[11] Patent Number: 4,873,019

[45] Date of Patent: Oct. 10, 1989

[54] CYCLOPENTANE DERIVATIVES

[75] Inventors: Joachim Krause, Dieburg; Andreas Wächtler, Griescheim, both of Fed. Rep. of Germany; Bernard Scheuble, Yokohama, Japan; Georg Weber, Erzhausen, Fed. Rep. of Germany

[73] Assignee: Merck Patent Gesellschaft mit Beschrankter Haftung, Darmstadt, Fed. Rep. of Germany

[21] Appl. No.: 135,103

[22] Filed: Dec. 18, 1987

[30] Foreign Application Priority Data

Dec. 20, 1986 [DE] Fed. Rep. of Germany ....... 3643795

[51] Int. Cl.$^4$ .................. G02F 1/13; C09K 19/30; C07C 69/74; C07C 69/773; C07C 43/21
[52] U.S. Cl. ............... 252/299.61; 252/299.6; 252/299.5; 252/299.63; 252/299.62; 350/350 R
[58] Field of Search ............... 252/299.61, 299.63, 252/299.6, 299.5, 299.62, 299.64, 299.65, 299.66, 299, 67, 299.68; 350/350 R, 350 S

[56] References Cited

U.S. PATENT DOCUMENTS 4,224,324  9/1980  Welch, Jr. ................ 424/256

FOREIGN PATENT DOCUMENTS

| | | |
|---|---|---|
| 3604898 | 8/1987 | Fed. Rep. of Germany ............ 252/299.61 |
| 3604899 | 8/1987 | Fed. Rep. of Germany ............ 252/299.61 |
| 55-149372 | 11/1980 | Japan ............ 252/299.61 |
| 55-151077 | 11/1980 | Japan ............ 252/299.61 |
| 56-36566 | 4/1981 | Japan ............ 252/299.63 |
| 60-209539 | 10/1985 | Japan ............ 252/299.62 |
| 63-304088 | 12/1988 | Japan ............ 252/299.61 |

OTHER PUBLICATIONS

Osman, M. A. et al., Mol. Cryst. Liq. Cryst., vol. 82 (Lett), pp. 339–344 (1983).
Ehlinger, E. et al., J. Am. Chem. Soc., vol. 102, pp. 5004–5011 (1980).
Demus, D. et al., Flussile Kristalle in Tabellen II, Veb Deutscher Velag Fur Grundstoff Industrie, Leipzig, pp. 345, 349–356.
Zaschke, H. et al., Liquid Crystals and Ordered Fluids, vol. 4, Griffin, A. et al., Ed., Plenum Press, N.Y., pp. 75–87 (1984).

*Primary Examiner*—Teddy S. Gron
*Attorney, Agent, or Firm*—Millen, White & Zelano

[57] ABSTRACT

1,3-Cyclopentylene compounds of the formula I $$R^1\text{-}A^1\text{-}Z^1\text{-}A^2\text{-}(Z^2\text{-}A^3)_n\text{-}R^2 \qquad \text{I}$$

in which $R^1$, $R^2$, $A^1$, $A^2$, $A^3$, $Z^1$, $Z^2$ and n have the meaning given herein, can be used as components of liquid-crystalline phases.

15 Claims, No Drawings

CYCLOPENTANE DERIVATIVES

SUMMARY OF THE INVENTION

It is an object of this invention to provide novel stable liquid-crystalline or mesogenic compounds useful as components of liquid-crystalline phases.

These objects have been achieved by providing 1,3-cyclopentylene compounds of the formula I

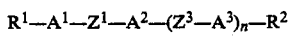

$$R^1-A^1-Z^1-A^2-(Z^3-A^3)_n-R^2$$

in which $R^1$ and $R^2$, in each case independently of one another, are an alkyl group having 1-15 carbon atoms in which, in addition, one or more non-neighbouring $CH_2$ groups can be replaced by —O—, —CO—, —O—CO—, —O—CO—O—, —CHhalogen—, —CHCN— and/or —CH=CH—, and one of the radicals $R^1$ and $R^2$ is alternatively F, Cl, Br, CN, COOH, OH, SH, $NH_2$, $NO_2$ or —NCS, $Z^1$ and $Z^2$, in each case independently of one another, are —CO—O—, —O—CO—, —$CH_2CH_2$—, —$CH_2$—O—, —$OCH_2$—, —N=N—, —NO=N—, —CH=N— or a single bond, and one of the groups $Z^1$ and $Z^2$ is alternatively —$CH_2$—, —O—, —CO—, —CHCN—, —CHhalogen—, —$CH_2CH_2CH_2$—, —$CH_2$—COO— or —$CH_2OCO$—, $A^1$, $A^2$ and $A^3$, in each case independently of one another, are a 1,4-phenylene group in which, in addition, one or more CH groups may be replaced by N, 1,4-cyclohexylene group in which, in addition, one or two non-neighbouring $CH_2$ groups may be replaced by O and/or S, 1,3-cyclopentylene group in which, in addition, one or two non-neighbouring $CH_2$ groups may be replaced by O and/or S, 1,4-bicyclo(2,2,2)octylene groups, piperidine-1,4-diyl group, naphthalene-2,6-diyl group, decahydronaphthalene-2,6-diyl group or 1,2,3,4-tetrahydronaphthalene-2,6-diyl group, each of which is unsubstituted or monosubstituted or polysubstituted by halogen, nitrile and/or alkyl, and n is 0, 1, 2 or 3, with the proviso that at least one of the rings $A^1$, $A^2$ and $A^3$ is 1,3-cyclopentylene in which, in addition, one or two non-neighbouring $CH_2$ groups may be replaced by O and/or S.

For reasons of simplicity, in the text below Cy is a 1,4-cyclohexylene group, Cyp is a 1,3-cyclopentylene group in which, in addition, one or two non-neighbouring $CH_2$ groups may be replaced by O and/or S, Dio is a 1,3-dioxane-2,5-diyl group, Dit is a 1,3-dithiane-2,5-diyl group, Bi is a bicyclo[2,2,2]octylene group, Pip is a piperidine-1,4-diyl group, Phe is a 1,4-phenylene group, Pyr is a pyrimidine-2,5-diyl group and Pyn is a pyridazine-3,6-diyl group, where Phe and/or Pyr and/or Pyn may be unsubstituted or substituted by one or two F and/or Cl atoms and/or $CH_3$ groups and/or CN groups.

The compounds of the formula I can be used as components of liquid-crystalline phases, in particular for displays which are based on the principle of twisted cells, the quest-host effect, the effect of deformation of aligned phases or the effect of dynamic scattering.

In addition, compounds of the formula I are suitable components of chirally tilted smectic phases.

Chirally tilted smectic liquid-crystalline phases having ferroelectric properties can be produced by adding a suitable chiral dope to basic mixtures having one or more tilted smectic phases (L.A. Veresnev et al., Mol. Cryst. Liq. Cryst. 89, 327 (1982); H. R. Brand et al., J. Physique 44 (Lett.), L-771 (1983)). Such phases can be used as dielectrics for fast-switching displays which are based on the principle, described by Clark and Lagerwall, of SSFLC technology (N. A. Clark and S. T. Lagerwall, Appl. Phys. Lett. 36, 899 (1980); U.S. Pat. No. 4,367,924) on the basis of the ferroelectric properties of the chirally tilted phase.

It has been found that the compounds of the formula I are highly suitable as components of liquid-crystalline phases. In particular, stable liquid-crystalline phases having a broad mesophase region and comparatively low viscosity can be produced with their aid.

In addition, the compounds of the formula I are suitable as components of chirally tilted smectic liquid-crystalline phases.

In addition, the range of liquid-crystalline substances which are suitable, under various applicational points of view, for the production of liquid-crystalline mixtures is, very generally, considerably extended through the provision of the compounds of the formula I.

The compounds of the formula I have a broad range of applications. Depending on the choice of substituents, these compounds can be used as base materials from which liquid-crystalline phases are in the main composed; however, it is also possible to add compounds of the formula I to liquid-crystalline base materials made from other classes of compounds in order, for example, to vary the dielectric and/or optical anisotropy and/or the viscosity and/or the spontaneous polarization and/or the phase regions and/or the tilt angle and/or the pitch of such a dielectric.

The compounds of the formula I are furthermore suitable as intermediates in the preparation of other substances which can be used as components of liquid-crystalline dielectrics.

In the pure state, the compounds of the formula I are colorless and form liquid-crystalline mesophases in a temperature range which is favorable for electro-optical use. They are very stable chemically, thermally and against light.

The invention thus relates to compounds of the formula I and to a process for the preparation of compounds of the formula I, characterized in that a compound which otherwise corresponds to the formula I, but contains, in place of H atoms, one or more reducible groups and/or C-C bonds, is treated with a reducing agent, or in that, for the preparation of compounds of the formula I in which $R^1$ or $R^2$ is F, Cl, Br or CN, the diazonium group in a corresponding diazonium salt is replaced by F, Cl, Br or CN, or in that, for the preparation of esters of the formula I (in which $Z^1$ and/or $Z^2$ are —CO—O— or —O—CO— and/or $R^1$ and/or $R^2$ contain a carboxyl group), an appropriate carboxylic acid or one of its reactive derivatives is reacted with an appropriate alcohol or one of its reactive derivatives, or in that, for the preparation of nitriles of the formula I (in which $R^1$ or $R^2$ is CN and/or which $A^1$ and/or $A^2$ and/or $A^3$ is substituted by at least one CN group), an appropriate carboxyamide is dehydrated or an appropriate carbonyl halide is reacted with sulfamide, or in that, for the preparation of ethers of the formula I (in which $R^1$ and/or $R^2$ is an alkoxy group and/or $Z^1$ and/or $Z^2$ is a —O $CH_2$— or —$CH_2O$— group), an appropriate hydroxyl compound is etherified, and/or in that, if appropriate, a chlorine and/or bromine compound of the formula I (in which $R^1$ and/or $R^2$ is Cl or Br and/or in which $A^1$ and/or $A^2$ and/or $A^3$ is substituted by at least one chlorine or bromine atom) is reacted with a cyanide.

The invention furthermore relates to the use of the compounds of the formula I as components of liquid-crystalline phases. The invention furthermore relates to liquid-crystalline phases containing at least one compound having the structural element 1,3-cyclopentylene in which, in addition, one or two non-neighbouring $CH_2$ groups may be replaced by O and/or S, in particular a compound of the formula I, and also to liquid-crystal display elements which contain such phases. Such phases have particularly advantageous elastic constants.

Above and below, $R^1$, $R^2$, $A^1$, $A^2$, $A^3$, $Z^1$, $Z^2$ and n have the meaning specified, unless expressly stated otherwise.

Accordingly, the compounds of the formula I cover compounds having two rings, of the subformulae Ia and Ib:

$R^1-A^1-Z^1-A^2-R^2$      Ia $R^1-A^1-A^2-R^2$      Ib, compounds having three rings, of the subformulae Ic to Ie:

$R^1-A^1-A^2-A^3-R^2$      Ic $R^1-A^1-Z^1-A^2-A^3-R^2$      Id $R^1-A^1-Z^1-A^2-Z^2-A^3-R^2$      Ie, compounds having four rings, of the subformulae If to Ik:

$R^1-A^1-A^2-A^3-A^3-R^2$      If $R^1-A^1-Z^1-A^2-A^3-A^3-R^2$      Ig $R^1-A^1-A^2-Z^2-A^3-A^3-R^2$      Ih $R^1-A^1-Z^1-A^2-Z^2-A^3-A^3-R^2$      Ii $R^1-A^1-Z^1-A^2-A^3-Z^2-A^3-R^2$      Ij $R^1-A^1-Z^1-A^2-Z^2-A^3-Z^2-A^3-R^2$      Ik and also compounds having five rings, of the subformulae Il to It:

$R^1-A^1-A^2-A^3-A^3-A^3-R^2$      Il $R^1-A^1-Z^1-A^2-A^3-A^3-A^3-R^2$      Im $R^1-A^1-A^2-Z^2-A^3-A^3-A^3-R^2$      In $R^1-A^1-Z^1-A^2-Z^2-A^3-A^3-A^3-R^2$      Io $R^1-A^1-Z^1-A^2-A^3-Z^2-A^3-A^3-R^2$      Ip $R^1-A^1-Z^1-A^2-A^3-A^3-Z^2-A^3-R^2$      Iq $R^1-A^1-Z^1-A^2-Z^2-A^3-Z^2-A^3-A^3-R^2$      Ir $R^1-A^1-Z^1-A^2-Z^2-A^3-A^3-Z^2-A^3-R^2$      Is $R^1-A^1-Z^1-A^2-Z^2-A^3-A^3-Z^2-A^3-Z^2-A^3-R^2$      It.

In the compounds of the formulae above and below, $R^1$ and $R^2$ are preferably alkyl, furthermore alkoxy.

Furthermore preferred are compounds of the formulae above and below in which one of the radicals $R^1$ and $R^2$ is CN, F or Cl.

$A^1$, $A^2$ and $A^3$ are preferably Cyp, Cy, Phe, Dio or Pyr; the compound of the formula I preferably does not contain more than one each of the radicals Dio, Dit, Pip, Bi, Pyn, Pyr, 1,3-cyclopentylene or hetero-substituted 1,3-cyclopentylene.

Subject to the proviso that at least one of the rings $A^1$, $A^2$ and $A^3$ is 1,3-cyclopentylene in which, in addition, one or two non-neighbouring $CH_2$ groups may be replaced by O and/or S, at least one of these rings may also be tetrahydrofuran-2,5-diyl, tetrahydrothiophene-2,5-diyl, 1,3-dioxolane-2,5-diyl, 1,3-dithiolane-2,5-diyl, 1,3-oxathiolane-2,4-diyl or 1,3-oxathiolane-2,5-diyl, tetrahydrofuran-2,5-diyl and/or 1,3-dioxolane-2,5-diyl are preferred here.

Preferably, only one of the rings $A^1$, $A^2$ and $A^3$ is a five-membered ring of the structure given above; 1,3-cyclopentylene is preferred here, in addition also tetrahydrofuran-2,5-diyl and/or 1,3-dioxolane-2,5-diyl.

$Z^1$ and $Z^2$ are preferably single bonds, and secondarily preferably —CO—O—, —O—CO— or —$CH_2CH_2$— groups.

If $R^1$ and $R^2$ are alkyl radicals and/or alkoxy radicals, they may be straight-chain or branched. They are preferably straight-chain, have 2, 3, 4, 5, 6 or 7 carbon atoms and accordingly are preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

The compounds of the formula I having branched wing groups $R^1$ or $R^2$ can occasionally be important due to better solubility in the conventional liquid-crystalline base materials, but in particular as chiral dopes if they are optically active.

Branched groups of this type generally contain no more than one chain branch. Preferred branched radicals $R^1$ and $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

Formula I covers the racemates of these compounds and the optical antipodes, and the mixtures thereof.

Of the compounds of the formulae I and Ia to It those are preferred in which at least one of the radicals contained therein has one of the preferred meanings specified. Particularly preferred smaller groups of compounds are those of the formulae I1 to I19:

$R^1$—Cyp—COO—Phe—$R^2$      I1

$R^1$—Cyp—$CH_2CH_2$—Phe—$R^2$      I2

$R^1$—Cyp—Phe—COO—Phe—$R^2$      I3

$R^1$—Cyp—Phe—$CH_2CH_2$—Phe—$R^2$      I4

$R^1$—Cyp—Phe—$CH_2CH_2$—Cy—$R^2$      I5

$R^1$—Cyp—Phe—$CH_2CH_2$—Phe—Cy—$R^2$      I6

$R^1$—Cyp—Phe—CH$_2$CH$_2$—Phe—Dio—$R^2$   I7

$R^1$—Cyp—Phe—$R^2$   I8

$R^1$—Cyp—Phe—Phe—$R^2$   I9

$R^1$—Cyp—Phe—Phe—Cy—$R^2$   I10

$R^1$—Cyp—Phe—Phe—Dio—$R^2$   I11

$R^1$—Cyp—Cy—Phe—$R^2$   I12

$R^1$—Cy—Cyp—Phe—$R^2$   I13

$R^1$—Cyp—Cy—$R^3$   I14

$R^1$—Cyp—Cy—Cy—$R^2$   I15

$R^1$—Cyp—Pyr—$R^2$   I16

$R^1$—Cyp—CH$_2$CH$_2$—Phe—Phe—$R^2$   I17

$R^1$—Cyp—CH$_2$CH$_2$—Phe—Phe—Cy—$R^2$   I18

$R^1$—Cyp—CH$_2$CH$_2$—Phe—Cy—$R^2$   I19

In the compounds of the formula I, those stereoisomers are preferred in which the rings Cy, Cyp, Dio, Dit and/or Pip are trans-disubstituted. Those of the above-mentioned formulae which contain one or more Dio, Dit, Pip and/or Pyr groups in each case include the two possible 2,5 (Dio, Dit and Pyr) or 1,4 (Pip) positional isomers. The Cy and Cyp rings are preferably unsubstituted; furthermore preferred are Cy and/or Cyp rings which are monosubstituted in the 1(4) (Cy) or 1(3) position by CN or C$_1$-C$_4$ alkyl.

Particularly preferred compounds of the formula I are those in which $R^1$ and $R^2$ are in each case straight-chain or at most monobranched alkyl groups or alkoxy groups having 1–10 carbon atoms, or CN.

Particularly preferred are the following smaller groups of compounds in which —A— is 1,3-cyclopentylene, tetrahydrofuran-2,5-diyl or 1,3-dioxolane-2,5-diyl, Phe is 1,4-phenylene, Cyc is 1,4-cyclohexylene, Dio is 1,3-dioxane-2,5-diyl and Pyr is pyrimidine-2,5-diyl, and Alkyl is preferably straight-chain methyl, ethyl, propyl, butyl, pentyl, hexyl, heptyl, octyl, nonyl or decyl; oxaalkyl is preferably straight-chain 2-oxypropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

I.
 Alkyl—A—Phe—CN
 Alkyl—A—Phe—methyl
 Alkyl—A—Phe—ethyl
 Alkyl—A—Phe—propyl
 Alkyl—A—Phe—butyl
 Alkyl—A—Phe—pentyl
 Alkyl—A—Phe—hexyl
 Alkyl—A—Phe—heptyl
 Alkyl—A—Phe—octyl
 Alkyl—A—Phe—nonyl
 Alkyl—A—Phe—decyl
II.
 Alkyl—A—Phe—methoxy
 Alkyl—A—Phe—ethoxy
 Alkyl—A—Phe—propoxy
 Alkyl—A—Phe—butoxy
 Alkyl—A—Phe—pentoxy
 Alkyl—A—Phe—hexoxy
 Alkyl—A—Phe—heptoxy
 Alkyl—A—Phe—octoxy
 Alkyl—A—Phe—nonoxy
 Alkyl—A—Phe—docoxy
 Alkyl—A—(3—F—Phe)—CN
III.
 Alkyl—A—Cyc—CN
 Alkyl—A—Cyc—methyl
 Alkyl—A—Cyc—ethyl
 Alkyl—A—Cyc—propyl
 Alkyl—A—Cyc—butyl
 Alkyl—A—Cyc—pentyl
 Alkyl—A—Cyc—hexyl
 Alkyl—A—Cyc—heptyl
 Alkyl—A—Cyc—octyl
 Alkyl—A—Cyc—nonyl
 Alkyl—A—Cyc—decyl
IV.
 Alkyl—A—Cyc—methoxy
 Alkyl—A—Cyc—ethoxy
 Alkyl—A—Cyc—propoxy
 Alkyl—A—Cyc—butoxy
 Alkyl—A—Cyc—pentoxy
 Alkyl—A—Cyc—hexoxy
 Alkyl—A—Cyc—heptoxy
 Alkyl—A—Cyc—octoxy
 Alkyl—A—Cyc—nonoxy
 Alkyl—A—Cyc—decoxy
V.
 Alkyl—A—Cyc—methoxycarbonyl
 Alkyl—A—Cyc—ethoxycarbonyl
 Alkyl—A—Cyc—propoxycarbonyl
 Alkyl—A—Cyc—butoxycarbonyl
 Alkyl—A—Cyc—pentoxycarbonyl
 Alkyl—A—Cyc—hexoxycarbonyl
 Alkyl—A—Cyc—heptoxycarbonyl
 Alkyl—A—Cyc—octoxycarbonyl
 Alkyl—A—Cyc—nonoxycarbonyl
 Alkyl—A—Cyc—decoxycarbonyl
VI.
 Alkyl—A—Cyc—methylcarbonyloxy
 Alkyl—A—Cyc—ethylcarbonyloxy
 Alkyl—A—Cyc—propylcarbonyloxy
 Alkyl—A—Cyc—butylcarbonyloxy
 Alkyl—A—Cyc—pentylcarbonyloxy
 Alkyl—A—Cyc—hexylcarbonyloxy
 Alkyl—A—Cyc—heptylcarbonyloxy
 Alkyl—A—Cyc—octylcarbonyloxy
 Alkyl—A—Cyc—nonylcarbonyloxy
 Alkyl—A—Cyc—pecylcarbonyloxy
VII.
 Methyl—A—Cyc—oxaalkyl
 Ethyl—A—Cyc—oxaalkyl
 Propyl—A—Cyc—oxaalkyl
 Butyl—A—Cyc—oxaalkyl
 Pentyl—A—Cyc—oxaalkyl
 Hexyl—A—Cyc—oxaalkyl
 Heptyl—A—Cyc—oxaalkyl
 Octyl—A—Cyc—oxaalkyl
 Nonyl—A—Cyc—oxaalkyl
 Decyl—A—Cyc—oxaalkyl
VIII.
 Alkyl—A—Phe—Phe—CN
 Alkyl—A—Phe—Phe—methyl
 Alkyl—A—Phe—Phe—ethyl Alkyl—A—Phe—Phe—propyl
Alkyl—A—Phe—Phe—butyl
Alkyl—A—Phe—Phe—pentyl
Alkyl—A—Phe—Phe—hexyl
Alkyl—A—Phe—Phe—heptyl
Alkyl—A—Phe—Phe—octyl
Alkyl—A—Phe—Phe—nonyl
Alkyl—A—Phe—Phe—decyl
Alkyl—A—Phe—(3—F—Phe)—CN IX.
Alkyl—A—Phe—Phe—methoxy
Alkyl—A—Phe—Phe—ethoxy
Alkyl—A—Phe—Phe—propoxy
Alkyl—A—Phe—Phe—butoxy
Alkyl—A—Phe—Phe—pentoxy
Alkyl—A—Phe—Phe—hexoxy
Alkyl—A—Phe—Phe—heptoxy
Alkyl—A—Phe—Phe—octoxy
Alkyl—A—Phe—Phe—nonoxy
Alkyl—A—Phe—Phe—decoxy X.
Alkyl—A—Cyc—Phe—CN
Alkyl—A—Cyc—Phe—methyl
Alkyl—A—Cyc—Phe—ethyl
Alkyl—A—Cyc—Phe—propyl
Alkyl—A—Cyc—Phe—butyl
Alkyl—A—Cyc—Phe—pentyl
Alkyl—A—Cyc—Phe—hexyl
Alkyl—A—Cyc—Phe—heptyl
Alkyl—A—Cyc—Phe—octyl
Alkyl—A—Cyc—Phe—nonyl
Alkyl—A—Cyc—Phe—decyl
Alkyl—A—Cyc—(3—F—Phe)—CN XI.
Alkyl—A—Cyc—Phe—methoxy
Alkyl—A—Cyc—Phe—ethoxy
Alkyl—A—Cyc—Phe—propoxy
Alkyl—A—Cyc—Phe—butoxy
Alkyl—A—Cyc—Phe—pentoxy
Alkyl—A—Cyc—Phe—hexoxy
Alkyl—A—Cyc—Phe—heptoxy
Alkyl—A—Cyc—Phe—octoxy
Alkyl—A—Cyc—Phe—nonoxy
Alkyl—A—Cyc—Phe—decoxy XII.
Alkyl—A—Cyc—Cyc—CN
Alkyl—A—Cyc—Cyc—methyl
Alkyl—A—Cyc—Cyc—ethyl
Alkyl—A—Cyc—Cyc—propyl
Alkyl—A—Cyc—Cyc—butyl
Alkyl—A—Cyc—Cyc—pentyl
Alkyl—A—Cyc—Cyc—hexyl
Alkyl—A—Cyc—Cyc—heptyl
Alkyl—A—Cyc—Cyc—octyl
Alkyl—A—Cyc—Cyc—nonyl
Alkyl—A—Cyc—Cyc—decyl XIII.
Alkyl—Cyc—A—Phe—CN
Alkyl—Cyc—A—Phe—methyl
Alkyl—Cyc—A—Phe—ethyl
Alkyl—Cyc—A—Phe—propyl
Alkyl—Cyc—A—Phe—butyl
Alkyl—Cyc—A—Phe—pentyl
Alkyl—Cyc—A—Phe—hexyl
Alkyl—Cyc—A—Phe—heptyl
Alkyl—Cyc—A—Phe—octyl
Alkyl—Cyc—A—Phe—nonyl
Alkyl—Cyc—A—Phe—decyl
Alkyl—Cyc—A—(3—F—Phe)—CN XIV.
Alkyl—Cyc—A—Phe—methoxy
Alkyl—Cyc—A—Phe—ethoxy
Alkyl—Cyc—A—Phe—propoxy
Alkyl—Cyc—A—Phe—butoxy
Alkyl—Cyc—A—Phe—pentoxy
Alkyl—Cyc—A—Phe—hexoxy
Alkyl—Cyc—A—Phe—heptoxy
Alkyl—Cyc—A—Phe—octoxy
Alkyl—Cyc—A—Phe—nonoxy
Alkyl—Cyc—A—Phe—decoxy XV.
Cyan—Cyc—Phe—Phe—A—alkyl
Methyl—Cyc—Phe—Phe—A—alkyl
Ethyl—Cyc—Phe—Phe—A—alkyl
Propyl—Cyc—Phe—Phe—A—alkyl
Butyl—Cyc—Phe—Phe—A—alkyl
Pentyl—Cyc—Phe—Phe—A—alkyl
Hexyl—Cyc—Phe—Phe—A—alkyl
Heptyl—Cyc—Phe—Phe—A—alkyl
Octyl—Cyc—Phe—Phe—A—alkyl
Nonyl—Cyc—Phe—Phe—A—alkyl
Decyl—Cyc—Phe—Phe—A—alkyl XVI.
Alkyl—A—Pyr—methyl
Alkyl—A—Pyr—ethyl
Alkyl—A—Pyr—propyl
Alkyl—A—Pyr—butyl
Alkyl—A—Pyr—pentyl
Alkyl—A—Pyr—hexyl
Alkyl—A—Pyr—heptyl
Alkyl—A—Pyr—octyl
Alkyl—A—Pyr—nonyl
Alkyl—A—Pyr—decyl XVII.
Alkyl—A—Pyr—Phe—CN XVIII.
Alkyl—A—COO—Phe—CN
Alkyl—A—COO—Phe—methyl
Alkyl—A—COO—Phe—ethyl
Alkyl—A—COO—Phe—propyl
Alkyl—A—COO—Phe—butyl
Alkyl—A—COO—Phe—pentyl
Alkyl—A—COO—Phe—hexyl
Alkyl—A—COO—Phe—heptyl
Alkyl—A—COO—Phe—octyl
Alkyl—A—COO—Phe—nonyl
Alkyl—A—COO—Phe—decyl XIX.
Alkyl—A—COO—Phe—methoxy
Alkyl—A—COO—Phe—ethoxy
Alkyl—A—COQ—Phe—propoxy
Alkyl—A—COO—Phe—butoxy
Alkyl—A—COO—Phe—pentoxy
Alkyl—A—COO—Phe—hexoxy
Alkyl—A—COO—Phe—heptoxy
Alkyl—A—COO—Phe—octoxy
Alkyl—A—COO—Phe—nonoxy
Alkyl—A—COO—Phe-decoxy XX.
Alkyl—A—COO—Cyc—CN
Alkyl—A—COO—Cyc—methyl
Alkyl—A—COO—Cyc—ethyl
Alkyl—A—COO—Cyc—propyl
Alkyl—A—COO—Cyc—butyl
Alkyl—A—COO—Cyc—pentyl
Alkyl—A—COO—Cyc—hexyl Alkyl—A—COO—Cyc—heptyl
Alkyl—A—COO—Cyc—octyl
Alkyl—A—COO—Cyc—nonyl
Alkyl—A—COO—Cyc—decyl XXI.
Alkyl—A—COO—Phe—Phe—CN
Alkyl—A—COO—Phe—Phe—methyl
Alkyl—A—COO—Phe—Phe—ethyl
Alkyl—A—COO—Phe—Phe—propyl
Alkyl—A—COO—Phe—Phe—butyl
Alkyl—A—COO—Phe—Phe—pentyl
Alkyl—A—COO—Phe—Phe—hexyl
Alkyl—A—COO—Phe—Phe—heptyl
Alkyl—A—COO—Phe—Phe—octyl
Alkyl—A—COO—Phe—Phe—nonyl
Alkyl—A—COO—Phe—Phe—decyl XXII.
Alkyl—A—Phe—COO—Cyc—CN
Alkyl—A—Phe—COO—Cyc—methyl
Alkyl—A—Phe—COO—Cyc—ethyl
Alkyl—A—Phe—COO—Cyc—propyl
Alkyl—A—Phe—COO—Cyc—butyl
Alkyl—A—Phe—COO—Cyc—pentyl
Alkyl—A—Phe—COO—Cyc—hexyl
Alkyl—A—Phe—COO—Cyc—heptyl
Alkyl—A—Phe—COO—Cyc—octyl
Alkyl—A—Phe—COO—Cyc—nonyl
Alkyl—A—Phe—COO—Cyc—decyl XXIII.
Alkyl—A—Phe—COO—Phe—CN
Alkyl—A—Phe—COO—Phe—methyl
Alkyl—A—Phe—COO—Phe—ethyl
Alkyl—A—Phe—COO—Phe—propyl
Alkyl—A—Phe—COO—Phe—butyl
Alkyl—A—Phe—COO—Phe—pentyl
Alkyl—A—Phe—COO—Phe—hexyl
Alkyl—A—Phe—COO—Phe—heptyl
Alkyl—A—Phe—COO—Phe—octyl
Alkyl—A—Phe—COO—Phe—nonyl
Alkyl—A—Phe—COO—Phe—decyl XXIV.
Alkyl—A—Phe—COO—Phe—methoxy
Alkyl—A—Phe—COO—Phe—ethoxy
Alkyl—A—Phe—COO—Phe—propoxy
Alkyl—A—Phe—COO—Phe—butoxy
Alkyl—A—Phe—COO—Phe—pentoxy
Alkyl—A—Phe—COO—Phe—hexoxy
Alkyl—A—Phe—COO—Phe—heptoxy
Alkyl—A—Phe—COO—Phe—octoxy
Alkyl—A—Phe—COO—Phe—nonoxy
Alkyl—A—Phe—COO—Phe—decoxy XXV.
Alkyl—A—Phe—COO—(3—F—Phe)—CN
Alkyl—A—Phe—CH2CH2—(3—F—Phe)—CN
Alkyl—A—Phe—CH2O—(3—F—Phe)—CN XXVI.
Alkyl—A—Cyc—COO—Cyc—CN
Alkyl—A—Cyc—COO—Cyc—methyl
Alkyl—A—Cyc—COO—Cyc—ethyl
Alkyl—A—Cyc—COO—Cyc—propyl
Alkyl—A—Cyc—COO—Cyc—butyl
Alkyl—A—Cyc—COO—Cyc—pentyl
Alkyl—A—Cyc—COO—Cyc—hexyl
Alkyl—A—Cyc—COO—Cyc—heptyl
Alkyl—A—Cyc—COO—Cyc—octyl
Alkyl—A—Cyc—COO—Cyc—nonyl
Alkyl—A—Cyc—COO—Cyc—decyl XXVII.
Alkyl—A—Cyc—COO—Phe—Cn
Alkyl—A—Cyc—COO—Phe—methyl
Alkyl—A—Cyc—COO—Phe—ethyl
Alkyl—A—Cyc—COO—Phe—propyl
Alkyl—A—Cyc—COO—Phe—butyl
Alkyl—A—Cyc—COO—Phe—pentyl
Alkyl—A—Cyc—COO—Phe—hexyl
Alkyl—A—Cyc—COO—Phe—heptyl
Alkyl—A—Cyc—COO—Phe—octyl
Alkyl—A—Cyc—COO—Phe—nonyl
Alkyl—A—Cyc—COO—Phe—decyl XXVIII.
Alkyl—A—Cyc—COO—Phe—methoxy
Alkyl—A—Cyc—COO—Phe—ethoxy
Alkyl—A—Cyc—COO—Phe—propoxy
Alkyl—A—Cyc—COO—Phe—butoxy
Alkyl—A—Cyc—COO—Phe—pentoxy
Alkyl—A—Cyc—COO—Phe—hexoxy
Alkyl—A—Cyc—COO—Phe—heptoxy
Alkyl—A—Cyc—COO—Phe—octoxy
Alkyl—A—Cyc—COO—Phe—nonoxy
Alkyl—A—Cyc—COO—Phe—decoxy XXIX.
Alkyl—A—OCO—Cyc—methyl
Alkyl—A—OCO—Cyc—ethyl
Alkyl—A—OCO—Cyc—propyl
Alkyl—A—OCO—Cyc—butyl
Alkyl—A—OCO—Cyc—pentyl
Alkyl—A—OCO—Cyc—hexyl
Alkyl—A—OCO—Cyc—heptyl
Alkyl—A—OCO—Cyc—octyl
Alkyl—A—OCO—Cyc—nonyl
Alkyl—A—OCO—Cyc—decyl XXX.
Alkyl—A—OCO—Phe—methyl
Alkyl—A—OCO—Phe—ethyl
Alkyl—A—OCO—Phe—propyl
Alkyl—A—OCO—Phe—butyl
Alkyl—A—OCO—Phe—pentyl
Alkyl—A—OCO—Phe—hexyl
Alkyl—A—OCO—Phe—heptyl
Alkyl—A—OCO—Phe—octyl
Alkyl—A—OCO—Phe—nonyl
Alkyl—A—OCO—Phe—decyl XXXI.
Alkyl—A—OCO—Phe—methoxy
Alkyl—A—OCO—Phe—ethoxy
Alkyl—A—OCO—Phe—propoxy
Alkyk—A—OCO—Phe—butoxy
Alkyl—A—OCO—Phe—pentoxy
Alkyl—A—OCO—Phe—hexoxy
Alkyl—A—OCO—Phe—heptoxy
Alkyl—A—OCO—Phe—octoxy
Alkyl—A—OCO—Phe—nonoxy
Alkyl—A—OCO—Phe—decoxy XXXII.
Alkyl—A—OCO—Dio—methyl
Alkyl—A—OCO—Dio—ethyl
Alkyl—A—OCO—Dio—propyl
Alkyl—A—OCO—Dio—butyl
Alkyl—A—OCO—Dio—pentyl
Alkyl—A—OCO—Dio—hexyl
Alkyl—A—OCO—Dio—heptyl
Alkyl—A—OCO—Dio—octyl
Alkyl—A—OCO—Dio—nonyl
Alkyl—A—OCO—Dio—decyl XXXIII.
Alkyl—A—CH2CH2—Phe—Phe—CN Alkyl—A—CH₂CH₂—Phe—Phe—methyl
Alkyl—A—CH₂CH₂—Phe—Phe—ethyl
Alkyl—A—CH₂CH₂—Phe—Phe—propyl
Alkyl—A—CH₂CH₂—Phe—Phe—butyl
Alkyl—A—CH₂CH₂—Phe—Phe—pentyl
Alkyl—A—CH₂CH₂—Phe—Phe—hexyl
Alkyl—A—CH₂CH₂—Phe—Phe—heptyl
Alkyl—A—CH₂CH₂—Phe—Phe—octyl
Alkyl—A—CH₂CH₂—Phe—Phe—nonyl
Alkyl—A—CH₂CH₂—Phe—Phe—decyl XXXIV.
Alkyl—A—CH₂CH₂—Phe—(2—F—Phe)—CN
Alkyl—A—CH₂CH₂—Phe—(2—F—Phe)—methyl
Alkyl—A—CH₂CH₂—Phe—(2—F—Phe)—ethyl
Alkyl—A—CH₂CH₂—Phe—(2—F—Phe)—propyl
Alkyl—A—CH₂CH₂—Phe—(2—F—Phe)—butyl
Alkyl—A—CH₂CH₂—Phe—(2—F—Phe)—pentyl
Alkyl—A—CH₂CH₂—Phe—(2—F—Phe)—hexyl
Alkyl—A—CH₂CH₂—Phe—(2—F—Phe)—heptyl
Alkyl—A—CH₂CH₂—Phe—(2—F—Phe)—octyl
Alkyl—A—CH₂CH₂—Phe—(2—F—Phe)—nonyl
Alkyl—A—CH₂CH₂—Phe—(2—F—Phe)—decyl XXXV.
Alkyl—A—CH₂CH₂—Phe—(2—F—Phe)—methoxy
Alkyl—A—CH₂CH₂—Phe—(2—F—Phe)—ethoxy
Alkyl—A—CH₂CH₂—Phe—(2—F—Phe)—propoxy
Alkyl—A—CH₂CH₂—Phe—(2—F—Phe)—butoxy
Alkyl—A—CH₂CH₂—Phe—(2—F—Phe)—pentoxy
Alkyl—A—CH₂CH₂—Phe—(2—F—Phe)—hexoxy
Alkyl—A—CH₂CH₂—Phe—(2—F—Phe)—heptoxy
Alkyl—A—CH₂CH₂—Phe—(2—F—Phe)—octoxy
Alkyl—A—CH₂CH₂—Phe—(2—F—Phe)—nonoxy
Alkyl—A—CH₂CH₂—Phe—(2—F—Phe)—decoxy XXXVI.
Alkyl—A—CH₂O—Phe—Pyr—methyl
Alkyl—A—CH₂O—Phe—Pyr—ethyl
Alkyl—A—CH₂O—Phe—Pyr—propyl
Alkyl—A—CH₂O—Phe—Pyr—butyl
Alkyl—A—CH₂O—Phe—Pyr—pentyl
Alkyl—A—CH₂O—Phe—Pyr—hexyl
Alkyl—A—CH₂O—Phe—Pyr—heptyl
Alkyl—A—CH₂O—Phe—Pyr—octyl
Alkyl—A—CH₂O—Phe—Pyr—nonyl
Alkyl—A—CH₂O—Phe—Pyr—decyl XXXVII.
Alkyl—A—CH₂CH₂—Cyc—CN
Alkyl—A—CH₂CH₂—Cyc—methyl
Alkyl—A—CH₂CH₂—Cyc—ethyl
Alkyl—A—CH₂CH₂—Cyc—propyl
Alkyl—A—CH₂CH₂—Cyc—butyl
Alkyl—A—CH₂CH₂—Cyc—pentyl
Alkyl—A—CH₂CH₂—Cyc—hexyl
Alkyl—A—CH₂CH₂—Cyc—heptyl
Alkyl—A—CH₂CH₂—Cyc—octyl
Alkyl—A—CH₂CH₂—Cyc—nonyl
Alkyl—A—CH₂CH₂—Cyc—decyl The compounds of the formula I are prepared by methods which are known per se, as described in the literature (e.g. in the standard works such as Houben-Weyl, Methoden der Organischen Chemie [Methods of Organic Chemistry], Georg-Thieme-Verlag, Stuttgart), that is under reaction conditions which are known and suitable for the reactions mentioned. Use can also be made here of variants, not described in greater detail here, which are known per se.

The starting materials can also be formed in situ, if desired, by not isolating them from the reaction mixture, but instead further reacting them to form compounds of the formula I.

Thus, the compounds of the formula I can be prepared by reducing a compound which otherwise corresponds to the formula I, but contains one or more reducible groups and/or C—C bonds in place of H atoms.

Possible reducible groups are preferably carbonyl groups, in particular keto groups, furthermore, for example, free or esterified hydroxyl groups or aromatically bound halogen atoms. Preferred starting materials for the reduction correspond to the formula I, but can contain a cyclohexane ring or cyclohexanone ring in place of a cyclohexane ring and/or a —CH=CH— group in place of a —CH₂CH₂— group and/or a —CO— group in place of a —CH₂— group and/or a free or functionally derived (for example in the form of its p-toluenesulfonate) OH group in place of an H atom.

The reduction can take place, for example, through catalytic hydrogenation at temperatures between about 0° and about 200°, and at pressures between about 1 and 200 bar, in an inert solvent, for example an alcohol such as methanol, ethanol or isopropanol, an ether such as tetrahydrofuran (THF) or dioxane, an ester such as ethyl acetate, a carboxylic acid such as acetic acid or a hydrocarbon such as cyclohexane. Suitable catalysts are preferably noble metals such as Pt or Pd, which can be employed in the form of oxides (for example PtO₂ or PdO), on a support (for example Pd on charcoal, calcium carbonate or strontium carbonate) or in finely divided form.

Ketones can also be reduced by the methods of Clemmensen (using zinc, zinc amalgam or tin and hydrochloric acid, preferably in aqueous-alcoholic solution or in the heterogeneous phase using water/toluene at temperatures between about 80° and 120°) or Wolff-Kishner (using hydrazine, preferably in the presence of alkali such as KOH or NaOH, in a high-boiling solvent such as diethylene glycol or triethylene glycol, at temperatures between about 100° and 200°) to form the corresponding compounds of the formula I which contain alkyl groups and/or —CH₂CH₂ bridges.

In addition, reductions using complex hydrides are possible. For example, arylsulfonyloxy groups can be removed reductively using LiAlH₄, in particular p-toluenesulfonyloxymethyl groups can be reduced to methyl groups, preferably in an inert solvent such as diethyl ether or THF, at temperatures between about 0° and 100°. Double bonds can be hydrogenated (even in the presence of CN groups) using NaBH₄ or tributyltin hydride in methanol.

Esters of the formula I can also be obtained through esterification of appropriate carboxylic acids (or their reactive derivatives) using alcohols or phenols (or their reactive derivatives).

Suitable reactive derivatives of the carboxylic acids mentioned are, in particular, the acyl halides, above all the chlorides and bromides, furthermore the anhydrides, for example also mixed anhydrides, azides or esters, in particular alkyl esters having 1–4 carbon atoms in the alkyl group.

Possible reactive derivatives of the alcohols or phenols mentioned are, in particular, the corresponding metal alcoholates or phenolates, preferably of an alkali metal such as Na or K.

The esterification is advantageously carried out in the presence of an inert solvent. Highly suitable are, in particular, ethers such as diethyl ether, di-n-butyl ether, THF, dioxane or anisole, ketones such as acetone, butanone or cyclohexanone, amides such as DMF or hexamethylphosphoric triamide, hydrocarbons such as benzene, toluene or xylene, halogenated hydrocarbons such as carbon tetrachloride or tetrachloroethylene and sulfoxides such as dimethyl sulfoxide or sulfolane. Water-immiscible solvents can at the same time advantageously be used for azeotropic removal by distillation of the water formed during the esterification. Occasionally, it is also possible to use an excess of an organic base, for example pyridine, quinoline or triethylamine, as solvent for the esterification. The esterification can also be carried out in the absence of a solvent, for example by simply heating the components in the presence of sodium acetate. The reaction temperature is usually between $-50°$ and $+250°$, preferably between $-20°$ and $+80°$. At these temperatures, the esterification reactions are generally complete after 15 minutes to 48 hours.

The individual reaction conditions for the esterification depend substantially on the nature of the starting materials used. Thus, the reaction between a free carboxylic acid and a free alcohol or phenol is generally carried out in the presence of a strong acid, for example a mineral acid such as hydrochloric acid or sulfuric acid. A preferred reaction procedure is to react an acyl anhydride or, in particular, an acyl chloride with an alcohol, preferably in a basic medium, important bases being, in particular, alkali metal hydroxides such as sodium hydroxide or potassium hydroxide, alkali metal carbonate or hydrogen carbonates such as sodium carbonate, sodium hydrogen carbonate, potassium carbonate or potassium hydrogen carbonate, alkali metal acetates such as sodium acetate or potassium acetate, alkaline-earth metal hydroxides such as calcium hydroxide, or organic bases such as triethylamine, pyridine, lutidine, collidine or quinoline. A further preferred embodiment of the esterification comprises initially converting, for example through treatment with ethanolic sodium hydroxide solution or potassium hydroxide solution, the alcohol or phenol into the sodium or potassium alcoholate or phenolate, isolating and suspending the latter with sodium hydrogen carbonate or potassium carbonate while stirring in acetone or diethyl ether, and adding a solution of the acyl chloride or anhydride in diethyl ether, acetone or DMF to this suspension, preferably at temperatures between about $-25°$ and $+20°$.

In order to prepare nitriles of the formula I (in which $R^1$ and/or $R^2$ is CN and/or in which $A^1$, $A^2$ and/or $A^3$ is substituted by at least one CN group), appropriate acid amides, for example those in which a $CONH_2$ group replaces the X radical, can be dehydrated. The amides can be obtained, for example, from appropriate esters or acyl halides through reaction with ammonia. Suitable dehydrating agents are, for example, inorganic acid chlorides such as $SOCl_2$, $PCl_3$, $PCl_5$, $POCl_3$, $SO_2Cl_2$, $COCl_2$, furthermore $P_2O_5$, $P_2S_5$, $AlCl_3$ (for example as a double compound with NaCl), aromatic sulfonic acids and sulfonyl halides. This dehydration can be carried out in the presence or absence of an inert solvent, at temperatures between about $0°$ and $150°$; possible solvents are, for example, bases such as pyridine or triethylamine, aromatic hydrocarbons such as benzene, toluene or xylene, or amides such as DMF.

In order to prepare the abovementioned nitriles of the formula I, appropriate acyl halides, preferably the chlorides, can also be reacted with sulfamide, preferably in an inert solvent such as tetramethylene sulfone, at temperatures between about $80°$ and $150°$, preferably at $120°$. After conventional work-up, the nitriles can be isolated directly.

Ethers of the formula I (in which $R^1$ and/or $R^2$ is an alkoxy group and/or in which $Z^1$ and/or $Z^2$ is a $-OCH_2-$ or a $-CH_2O-$ group) can be obtained through etherification of appropriate hydroxyl compounds, preferably appropriate phenols, the hydroxyl compound preferably being converted initially into a corresponding metal derivative, for example through treatment with NaH, $NaNH_2$, NaOH, KOH, $Na_2CO_3$ or $K_2CO_3$ into the corresponding alkali metal alcoholate or alkali metal phenolate. The latter can then be reacted with the appropriate alkyl halide or sulfonate or dialkyl sulfate, preferably in an inert solvent such as acetone, 1,2-dimethoxyethane, DMF or dimethyl sulfoxide, or alternatively in an excess of aqueous or aqueous-alcoholic NaOH or KOH, at temperatures between about $20°$ and $100°$.

To prepare nitriles of the formula I (in which $R^1$ and/or $R^2$ are CN and/or in which $A^1$, $A^2$ and/or $A^3$ is substituted by at least one CN group), appropriate chlorine or bromine compounds of the formula I (in which $R^1$ and/or $R^2$ are Cl or Br and/or in which $A^1$, $A^2$ and/or $A^3$ is substituted by at least one Cl or Br atom) can also be reacted with a cyanide, preferably with a metal cyanide such as NaCN, KCN or $Cu_2(CN)_2$, for example in the presence of pyridine in an inert solvent such as DMF or N-methylpyrrolidone, at temperatures between $20°$ and $200°$.

Compounds of the formula I in which $R^1$ and/or $R^2$ are F, Cl, Br or CN can also be obtained from the corresponding diazonium salts through replacement of the diazonium group by a fluorine, chlorine or bromine atom or by a CN group, for example by the methods of Schiemann or Sandmeyer.

The diazonium salts can be prepared, for example, through nitration of compounds which correspond to the formula I, but contain one (or two) hydrogen atom(s) in place of the $R^1$ and/or $R^2$ radicals, reduction to the corresponding amines, and diazotization, for example using $NaNO_2$ or $KNO_2$, in aqueous solution at temperatures between about $-10°$ and $+10°$.

For the replacement of the diazonium group by fluorine, the diazotization can be carried out in anhydrous hydrofluoric acid with subsequent warming, or a reaction with tetrafluoroboric acid is carried out to give the diazonium tetrafluoroborate, which are subsequently thermally decomposed.

Replacement by Cl, Br or CN is preferably carried out through reaction of the aqueous diazonium salt solution with $Cu_2Cl_2$, $Cu_2Br_2$ or $Cu_2(CN)_2$ by the method of Sandmeyer.

A base of the formula I can be converted into the pertinent acid-addition salt using an acid. In this reaction, inorganic acids, for example sulfuric acid, nitric acid, hydrohalic acides such as hydrochloric acid or hydrobromic acid, phosphoric acids such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono and -di-sulfonic acids, and laurylsulfuric acid, can be used.

Conversely, it is possible to liberate the base of the formula I from an acid-addition salt of a compound of the formula I through treatment with a base, for example with a strong inorganic base such as KOH or NaOH.

The liquid-crystalline phases according to the invention comprise 2 to 25, preferably 3 to 15, components, including at least one compound of the formula I. The other components are preferably selected from nematic or nematogenic substances, in particular known substances from the classes comprising the azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexylpyrimidines, phenyl- or cyclohexyldioxanes, phenyl- or cyclohexyldithianes, 1,2-bis-phenylethanes, 1,2-bis-cyclohexylethanes, 1-phenyl-2-cyclohexylethanes, optionally halogenated stilbenes, benzyl phenyl ethers, tolanes and substituted cinnamic acids.

The most important compounds which are suitable as components of such liquid-crystalline phases can be characterized by the formula II

R'—L—G—E—R''    II in which L and E are each a carbo- or heterocyclic ring system from the group formed by 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydronaphthalene, quinazoline and tetrahydoquinazoline, G is

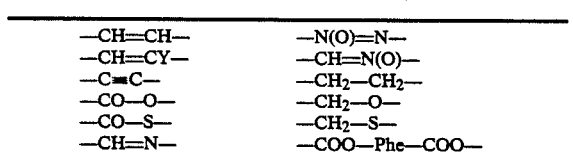

| —CH=CH— | —N(O)=N— |
| —CH=CY— | —CH=N(O)— |
| —C≡C— | —CH$_2$—CH$_2$— |
| —CO—O— | —CH$_2$—O— |
| —CO—S— | —CH$_2$—S— |
| —CH=N— | —COO—Phe—COO— | or a C—C single bond, Y is halogen, preferably chlorine or —CN, and R' and R'' are alkyl, alkoxy, alkanoyloxy or alkoxycarbonyloxy having up to 18, preferably up to 8, carbon atoms, or one of these radicals is alternatively CN, NC, NO$_2$, CF$_3$, F, Cl or Br.

In most of these compounds, R' and R'' are different from one another, and one of these radicals is usually an alkyl or alkoxy group. However, other variations of the proposed substituents are customary. Many such substances, or also mixtures thereof, are commercially available. All these substances can be prepared by methods which are known from the literature.

The liquid-crystalline phases according to the invention contain about 0.1 to 99, preferably 10 to 95, % of one or more compounds of the formula I. Further preferred liquid-crystalline phases are those which contain 0.1-50, in particular 0.5-30, % of one or more compounds of the formula I. Isotropic compounds of the formula I can also be used in the phases according to the invention.

The liquid-crystalline phases according to the invention are produced in a fashion which is conventional per se. In general, the components are dissolved in one another, preferably at elevated temperature.

By means of suitable additives, the liquid-crystalline phases can be modified according to the invention so that they can be used in all types of liquid-crystal display elements which have hitherto become known.

Such additives are known to those skilled in the art and are described in detail in the literature. For example, conducting salts, preferably ethyldimethyldodecylammonium 4-hexyloxybenzoate, tetrabutylammonium tetraphenylboranate or complex salts of crown ethers (cf. for example, I. Haller et al., Mol. Cryst. Liq. Cryst. volume 24, pages 249-258 (1973)) can be added in order to improve the conductivity, and dichroic dyestuffs in order to produce coloured guest-host systems, or substances for modifying the dielectric anisotropy, the viscosity and/or the orientation of the nematic phases. Such substances are described, for example, in German Offenlegungsschriften Nos. 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight. M.p.=melting point, c.p.=clear point.

The entire text of all applications, patents and publications, if any, cited above and below are hereby incorporated by reference.

EXAMPLE 1

4.1 g of 4-n-octylphenol and 1.6 g of pyridine are dissolved in 10 ml of toluene, the solution is warmed to 100°, 5.0 g of 4-(trans-3-n-propylcyclopentyl)benzoyl chloride (cf. Example 2) are added dropwise, and the mixture is left to react for 3 hours. The pyridine hydrochloride is subsequently filtered off under suction, and the filtrate is washed with water, dried and freed from solvent in vacuo. After crystallization of the residue from petroleum ether, 4-octylphenyl 4-(trans-3-propylcyclopentyl)-benzoate is obtained; m.p. 36°, c.p. 40.7°.

The compounds mentioned in group XXII are obtained analogously.

EXAMPLE 2

In corresponding fashion to the procedure given in Example 1, 4'-propylbiphenylyl 4-(trans-3-propylcyclopentyl)-benzoate is obtained from 4-(trans-3-n-propylcyclopentyl)-benzoyl chloride (prepared from 4-propylcyclohexanone through oxidation using nitric acid to give 3-propyladipic acid, cyclization of its barium salt to give 3-propylcyclopentanone, addition of phenyllithium, dehydration and hydrogenation to give 3-propylphenylcyclopentane, Friedel-Crafts acylation using acetyl chloride/aluminium chloride, and haloform degradation of the 4-(3-propylcyclopentyl)-acetophenone obtained to give 4-(3-propylcyclopentyl)-benzoic acid, and reaction of the latter with thionyl chloride) and 4-n-propyl-4'-hydroxybiphenyl; m.p. 90°, c.p. 190.1°.

The compounds mentioned in groups XXI, XXII, XXIV and XXV are prepared in a corresponding fashion.

EXAMPLE 3

4.0 g of trans-3-n-pentylcyclopentanecarbonyl chloride (obtainable from 5-n-pentylcyclohexanone through chlorination, Faworski rearrangement of the α-chloroketone using sodium alcoholate in ether, hydrolysis of the ethyl 3-n-pentylcyclopentanecarboxylate, alkaline isomerization of the acid and subsequent reaction with thionyl chloride) are added dropwise at 100° to a solution of 4.4 g of 4-(trans-4-n-propylcyclohexyl)-phenol and 1.6 g of pyridine in 10 ml of toluene. The mixture is allowed to react for a further 3 hours, the pyridine hydrochloride is filtered off under suction, the filtrate is washed with water and dried, and the solvent is evaporated. The residue is crystallized from ethanol. 4-(trans-4-propylcyclohexyl)-phenyl trans-3-pentylcyclopentanecarboxylate is obtained; smectic B/isotropic phase transition: 49°.

EXAMPLE 4

4-(trans-4-butylcyclohexyl)-phenyl trans-3-propylcyclopentanecarboxylate is obtained analogously to the procedure described in Example 3 using trans-3-n-propylcyclopentanecarbonyl chloride and 4-(trans-4-n-butylcyclohexyl)-phenol; m.p. 90°, c.p. 55.5°.

EXAMPLE 5

32 ml of 15% n-butyllithium solution in hexane are added dropwise to a suspension of 18.07 g of 4-n-octyloxy-4'-bromobiphenyl in a mixture of toluene/tetrahydrofuran at −15°. After 15 minutes, a clear solution is obtained and a mixture of 6.31 g of 3-n-propylcyclopentanone and 25 ml of toluene/tetrahydrofuran is added dropwise. After the mixture has reacted for a further 16 hours at room temperature and after conventional work-up and column chromatography, 4-(1-hydroxy-3-n-propylcyclopentyl)-4-n-octyloxybiphenyl is obtained.

From this, crude 4-(3-propylcyclopentyl)-4'-n-octyloxybiphenyl is obtained by heating with toluene/p-toluenesulfonic acid on a water separator and subsequent catalytic hydrogenation of the cyclopentenyl compound. Repeated crystallization from ethanol gives the pure trans-compound in the form of colorless crystals; m.p. 84°, c.p. 88°.

The compounds mentioned in groups VIII and IX are obtained in analogous fashion.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A liquid-crystalline phase having at least two liquid-crystalline components, wherein at least one liquid-crystalline compound is of the formula $$R^1-A^1-Z^1-A^2-(Z^2-A^3)_n-R^2$$

wherein
$R^1$ and $R^2$, in each case independently of one another, are alkyl of 1-15 carbon atoms, or alkyl of 1-15 carbon atoms in which one or more non-adjacent $CH_2$ groups are replaced by —O—, —CO—, —O—CO—, —O—CO—O—, —CHhalogen—, —CHCN— and/or —CH=CH—, and one of $R^1$ and $R^2$ can also be F, Cl, CN, or —NCS, $Z^1$ and $Z^2$ in each case independently of one another, are —CO—O—, —O—CO—, —CH$_2$CH$_2$—, —CH$_2$—O—, —OCH$_2$—, —N=N—, —NO=N—, —CH=N or a single bond, and one of $Z^1$ and $Z^2$ can also be —CO—, $A^1$, $A^2$ and $A^3$ in each case independently of one another, are 1,4-phenylene, 1,4-phenylene in which one or more CH groups are replaced by N, 1,4-cyclohexylene, 1,4-cyclohexylene in which one or two non-adjacent CH$_2$ groups are replaced by O and/or S, 1,3-cyclopentylene, 1,3-cyclopentylene in which one or two non-adjacent CH$_2$ groups are replaced by O and/or S, 1,4-bicyclo-(2,2,2)-octylene, piperidine-1,4-diyl, naphthalene-2,6-diyl, decahydronaphthalene-2,6-diyl or 1,2,3,4-tetrahydronaphthalene-2,6-diyl, each of which can also be substituted by halogen, nitrile and/or alkyl, and n is 0, 1 or 2, with the proviso that at least one of the rings $A^1$, $A^2$ and $A^3$ is 1,3-cyclopentylene or 1,3-cyclopentylene in which one or two non-adjacent CH$_2$ groups are replaced by O and/or S.

2. A liquid-crystalline phase of claim 1, wherein said compound is in the formula $$R^1-A^1-Z^1-A^2-R^2.$$

3. A liquid-crystalline phase of claim 1, wherein said compound is of the formula $$R^1-A^1-Z^1-A^2-Z^2-A^3-R^2.$$

4. A liquid-crystalline phase of claim 1, wherein said compound is of the formula $$R^1-A^1-Z^1-A^2-Z^2-A^3-Z^2-A^3-R^2.$$

5. A liquid-crystalline phase of claim 1, wherein said compound is of the formula
$R^1$—Cyp—COO—Phe—$R^2$,
$R^1$—Cyp—CH$_2$CH$_2$—Phe—$R^2$,
$R^1$—Cyp—Phe—COO—Phe—$R^2$,
$R^1$—Cyp—Phe—CH$_2$CH$_2$—Phe—$R^2$,
$R^1$—Cyp—Phe—CH$_2$CH$_2$—Cy—$R^2$,
$R^1$—Cyp—Phe—CH$_2$CH$_2$—Phe—Cy—$R^2$,
$R^1$—Cyp—Phe—CH$_2$CH$_2$—Phe—Dio—$R^2$,
$R^1$—Cyp—Phe—$R^2$,
$R^1$—Cyp—Phe—Phe—$R^2$,
$R^1$—Cyp—Phe—Phe—Cy—$R^2$,
$R^1$—Cyp—Phe—Phe—Dio—$R^2$,
$R^1$—Cyp—Cy—Phe—$R^2$,
$R^1$—Cy—Cyp—Phe—$R^2$,
$R^1$—Cyp—Cy—$R^3$,
$R^1$—Cyp—Cy—Cy—$R^2$,
$R^1$—Cyp—Pyr—$R^2$,
$R^1$—Cyp—CH$_2$CH$_2$—Phe—Phe—$R^2$,
$R^1$—Cyp—CH$_2$CH$_2$—Phe—Phe—Cy—$R^2$ or
$R^1$—Cyp—CH$_2$CH$_2$—Phe—Cy—$R^2$ wherein
Cyp is 1,3-cyclopentylene in which one or two non-neighboring CH$_2$-groups may be replaced by O and/or S;

Phe is 1,4-phenylene which is unsubstituted or substituted by one or two F and/or Cl atoms and/or CH$_3$-groups and/or CN groups;

Cy is 1,4-cyclohexylene; and

Pyr is pyrimidine-2,5-diyl which is unsubstituted or substituted by one or two F and/or Cl atoms and/or CH$_3$-groups and/or CN groups.

6. A liquid-crystalline phase of claim 1, wherein said compound is of the formula I.
Alkyl—A—Phe—CN
Alkyl—A—Phe—methyl
Alkyl—A—Phe—ethyl
Alkyl—A—Phe—propyl
Alkyl—A—Phe—butyl
Alkyl—A—Phe—pentyl
Alkyl—A—Phe—hexyl
Alkyl—A—Phe—heptyl
Alkyl—A—Phe—octyl
Alkyl—A—Phe—nonyl
Alkyl—A—Phe—decyl II.
Alkyl—A—Phe—methoxy
Alkyl—A—Phe—ethoxy
Alkyl—A—Phe—propoxy
Alkyl—A—Phe—butoxy
Alkyl—A—Phe—pentoxy
Alkyl—A—Phe—hexoxy
Alkyl—A—Phe—heptoxy
Alkyl—A—Phe—octoxy
Alkyl—A—Phe—nonoxy
Alkyl—A—Phe—decoxy
Alkyl—A—(3—F—Phe)—CN III.
Alkyl—A—Cyc—CN
Alkyl—A—Cyc—methyl
Alkyl—A—Cyc—ethyl
Alkyl—A—Cyc—propyl
Alkyl—A—Cyc—butyl
Alkyl—A—Cyc—pentyl
Alkyl—A—Cyc—hexyl
Alkyl—A—Cyc—heptyl
Alkyl—A—Cyc—octyl
Alkyl—A—Cyc—nonyl
Alkyl—A—Cyc—decyl IV.
Alkyl—A—Cyc—methoxy
Alkyl—A—Cyc—ethoxy
Alkyl—A—Cyc—propoxy
Alkyl—A—Cyc—butoxy
Alkyl—A—Cyc—pentoxy
Alkyl—A—Cyc—hexoxy
Alkyl—A—Cyc—heptoxy
Alkyl—A—Cyc—octoxy
Alkyl—A—Cyc—nonoxy
Alkyl—A—Cyc—decoxy V.
Alkyl—A—Cyc—methoxycarbonyl
Alkyl—A—Cyc—ethoxycarbonyl
Alkyl—A—Cyc—propoxycarbonyl
Alkyl—A—Cyc—butoxycarbonyl
Alkyl—A—Cyc—pentoxycarbonyl
Alkyl—A—Cyc—hexoxycarbonyl
Alkyl—A—Cyc—heptoxycarbonyl
Alkyl—A—Cyc—octoxycarbonyl
Alkyl—A—Cyc—nonoxycarbonyl
Alkyl—A—Cyc—decoxycarbonyl VI.
Alkyl—A—Cyc—methylcarbonyloxy
Alkyl—A—Cyc—ethylcarbonyloxy
Alkyl—A—Cyc—propylcarbonyloxy
Alkyl—A—Cyc—butylcarbonyloxy
Alkyl—A—Cyc—pentylcarbonyloxy
Alkyl—A—Cyc—hexylcarbonyloxy
Alkyl—A—Cyc—heptylcarbonyloxy
Alkyl—A—Cyc—octylcarbonyloxy
Alkyl—A—Cyc—nonylcarbonyloxy
Alkyl—A—Cyc—pecylcarbonyloxy VII.
Methyl—A—Cyc—oxaalkyl
Ethyl—A—Cyc—oxaalkyl
Propyl—A—Cyc—oxaalkyl
Butyl—A—Cyc—oxaalkyl
Pentyl—A—Cyc—oxaalkyl
Hexyl—A—Cyc—oxaalkyl
Heptyl—A—Cyc—oxaalkyl
Octyl—A—Cyc—oxaalkyl
Nonyl—A—Cyc—oxaalkyl
Decyl—A—Cyc—oxaalkyl VIII.
Alkyl—A—Phe—Phe—CN
Alkyl—A—Phe—Phe—methyl
Alkyl—A—Phe—Phe—ethyl
Alkyl—A—Phe—Phe—propyl
Alkyl—A—Phe—Phe—butyl
Alkyl—A—Phe—Phe—pentyl
Alkyl—A—Phe—Phe—hexyl
Alkyl—A—Phe—Phe—heptyl
Alkyl—A—Phe—Phe—octyl
Alkyl—A—Phe—Phe—nonyl
Alkyl—A—Phe—Phe—decyl
Alkyl—A—Phe—(3—F—Phe)—CN IX.
Alkyl—A—Phe—Phe—methoxy
Alkyl—A—Phe—Phe—ethoxy
Alkyl—A—Phe—Phe—propoxy
Alkyl—A—Phe—Phe—butoxy
Alkyl—A—Phe—Phe—pentoxy
Alkyl—A—Phe—Phe—hexoxy
Alkyl—A—Phe—Phe—heptoxy
Alkyl—A—Phe—Phe—octoxy
Alkyl—A—Phe—Phe—nonoxy
Alkyl—A—Phe—Phe—decoxy X.
Alkyl—A—Cyc—Phe—CN
Alkyl—A—Cyc—Phe—methyl
Alkyl—A—Cyc—Phe—ethyl
Alkyl—A—Cyc—Phe—propyl
Alkyl—A—Cyc—Phe—butyl
Alkyl—A—Cyc—Phe—pentyl
Alkyl—A—Cyc—Phe—hexyl
Alkyl—A—Cyc—Phe—heptyl
Alkyl—A—Cyc—Phe—octyl
Alkyl—A—Cyc—Phe—nonyl
Alkyl—A—Cyc—Phe—decyl
Alkyl—A—Cyc—(3—F—Phe)—CN XI.
Alkyl—A—Cyc—Phe—methoxy
Alkyl—A—Cyc—Phe—ethoxy
Alkyl—A—Cyc—Phe—propoxy
Alkyl'A—Cyc—Phe—butoxy
Alkyl—A—Cyc—Phe—pentoxy
Alkyl—A—Cyc—Phe—hexoxy
Alkyl—A—Cyc—Phe—heptoxy
Alkyl'A—Cyc—Phe—octoxy
Alkyl—A—Cyc—Phe—nonoxy Alkyl—A—Cyc—Phe—decoxy
XII.
  Alkyl—A—Cyc—Cyc—CN
  Alkyl—A-Cyc—Cyc—methyl
  Alkyl—A—Cyc—Cyc—ethyl
  Alkyl—A—Cyc—Cyc—propyl
  Alkyl—A—Cyc—Cyc—butyl
  Alkyl—A—Cyc—Cyc—Pentyl
  Alkyl—A—Cyc—Cyc—hexyl
  Alkyl—A—Cyc—Cyc—heptyl
  Alkyl—A—Cyc—Cyc—octyl
  Alkyl—A—Cyc—Cyc—nonyl
  Alkyl—A—Cyc—Cyc—decyl
XIII.
  Alkyl—Cyc—A—Phe—CN
  Alkyl—Cyc—A—Phe—methyl
  Alkyl—Cyc—A—Phe—ethyl
  Alkyl—Cyc—A—Phe—propyl
  Alkyl—Cyc—A—Phe—butyl
  Alkyl—Cyc—A—Phe—pentyl
  Alkyl—Cyc—A—Phe—hexyl
  Alkyl—Cyc—A—Phe—heptyl
  Alkyl—Cyc—A—Phe—octyl
  Alkyl—Cyc—A'Phe—nonyl
  Alkyl—Cyc—A—Phe—decyl
  Alkyl—Cyc—A—(3—F—Phe)—CN
XIV.
  Alkyl—Cyc—A—Phe—methoxy
  Alkyl—Cyc—A—Phe—ethoxy
  Alkyl—Cyc—A—Phe—propoxy
  Alkyl—Cyc—A—Phe—butoxy
  Alkyl—Cyc—A—Phe—pentoxy
  Alkyl—Cyc—A—Phe—hexoxy
  Alkyl—Cyc—A—Phe—heptoxy
  Alkyl—Cyc—A—Phe—octoxy
  Alkyl—Cyc—A—Phe—nonoxy
  Alkyl—Cyc—A—Phe—decoxy
XV.
  Cyan—Cyc—Phe—Phe'A—alkyl
  Methyl—Cyc—Phe—Phe—A—alkyl
  Ethyl—Cyc—Phe—Phe—A—alkyl
  Propyl—Cyc—Phe—Phe—A—alkyl
  Butyl—Cyc—Phe—Phe—A—alkyl
  Pentyl—Cyc—Phe—Phe—A—alkyl
  Hexyl—Cyc—Phe—Phe—A—alkyl
  Heptyl—Cyc—Phe—Phe—A—alkyl
  Octyl—Cyc—Phe—Phe—A—alkyl
  Nonyl—Cyc—Phe—Phe—A—alkyl
  Decyl—Cyc—Phe—Phe—A—alkyl
XVI.
  Alkyl—A—Pyr—methyl
  Alkyl—A—Pyr—ethyl
  Alkyl—A—Pyr—propyl
  Alkyl—A—Pyr—butyl
  Alkyl—A—Pyr—pentyl
  Alkyl—A—Pyr—hexyl
  Alkyl—A—Pyr—heptyl
  Alkyl—A—Pyr—octyl
  Alkyl—A—Pyr—nonyl
  Alkyl—A—Pyr—decyl
XVII.
  Alkyl—A—Pyr—Phe—CN
XVIII.
  Alkyl—A—COO—Phe—CN
  Alkyl—A—COO—Phe—methyl
  Alkyl—A—COO—Phe—ethyl
  Alkyl—A—COO—Phe—propyl
  Alkyl—A—COO—Phe—butyl
  Alkyl—A—COO—Phe—pentyl
  Alkyl—A—COO—Phe—hexyl
  Alkyl—A—COO—Phe—heptyl
  Alkyl—A—COO—Phe—octyl
  Alkyl—A—COO—Phe—nonyl
  Alkyl—A—COO—Phe—decyl
XIX.
  Alkyl—A—COO—Phe—methoxy
  Alkyl—A—COO—Phe—ethoxy
  Alkyl—A—COO—Phe—propoxy
  Alkyl—A—COO—Phe—butoxy
  Alkyl—A—COO—Phe—pentoxy
  Alkyl—A—COO—Phe—hexoxy
  Alkyl—A—COO—Phe—heptoxy
  Alkyl—A—COO—Phe—octoxy
  Alkyl—A—COO—Phe—nonoxy
  Alkyl—A—COO—Phe—decoxy
XX.
  Alkyl—A—COO—Cyc—CN
  Alkyl—A—COO—Cyc—methyl
  Alkyl—A—COO—Cyc—ethyl
  Alkyl—A—COO—Cyc—propyl
  Alkyl—A—COO—Cyc—butyl
  Alkyl—A—COO—Cyc—pentyl
  Alkyl—A—COO—Cyc—hexyl
  Alkyl—A—COO—Cyc—heptyl
  Alkyl—A—COO—Cyc—octyl
  Alkyl—A—COO—Cyc—nonyl
  Alkyl—A—COO—Cyc—decyl
XXI.
  Alkyl—A—COO—Phe—Phe—CN
  Alkyl—A—COO—Phe—Phe—methyl
  Alkyl—A—COO—Phe—Phe—ethyl
  Alkyl—A—COO—Phe—Phe—propyl
  Alkyl—A—COO—Phe—Phe—butyl
  Alkyl—A—COO—Phe—Phe—pentyl
  Alkyl—A—COO—Phe—Phe—hexyl
  Alkyl—A—COO—Phe—Phe—heptyl
  Alkyl—A—COO—Phe—Phe—octyl
  Alkyl—A—COO—Phe—Phe—nonyl
  Alkyl—A—COO—Phe—Phe—decyl
XXII.
  Alkyl—A—Phe—COO—Cyc—CN
  Alkyl—A—Phe—COO—Cyc—methyl
  Alkyl—A—Phe—COO—Cyc—ethyl
  Alkyl—A—Phe—COO—Cyc—propyl
  Alkyl—A—Phe—COO—Cyc—butyl
  Alkyl—A—Phe—COO—Cyc—pentyl
  Alkyl—A—Phe—COO—Cyc—hexyl
  Alkyl—A—Phe—COO—Cyc—heptyl
  Alkyl—A—Phe—COO—Cyc—octyl
  Alkyl—A—Phe—COO—Cyc—nonyl
  Alkyl—A—Phe—COO—Cyc—decyl
XXIII.
  Alkyl—A—Phe—COO—Phe—CN
  Alkyl—A—Phe—COO—Phe—methyl
  Alkyl—A—Phe—COO—Phe—ethyl
  Alkyl—A—Phe—COO—Phe—propyl
  Alkyl—A—Phe—COO—Phe—butyl
  Alkyl—A—Phe—COO—Phe—pentyl
  Alkyl—A—Phe—COO—Phe—hexyl
  Alkyl—A—Phe—COO—Phe—heptyl
  Alkyl—A—Phe—COO—Phe—octyl
  Alkyl—A—Phe—COO—Phe—nonyl
  Alkyl—A—Phe—COO—Phe—decyl
XXIV.
  Alkyl—A—Phe—COO—Phe—methoxy
  Alkyl—A—Phe—COO—Phe—ethoxy Alkyl—A—Phe—COO—Phe—propoxy
Alkyl—A—Phe—COO—Phe—butoxy
Alkyl—A—Phe—COO—Phe—pentoxy
Alkyl—A—Phe—COO—Phe—hexoxy
Alkyl—A—Phe—COO—Phe—heptoxy
Alkyl—A—Phe—COO—Phe—octoxy
Alkyl—A—Phe—COO—Phe—nonoxy
Alkyl—A—Phe—COO—Phe—decoxy
XXV.
   Alkyl—A—Phe—COO—(3—F—Phe)—CN
   Alkyl—A—Phe—CH$_2$CH$_2$—(3—F—Phe)—CN
   Alkyl—A—Phe—CH$_2$O—(3—F—Phe)—CN
XXVI.
   Alkyl—A—Cyc—COO—Cyc—CN
   Alkyl—A—Cyc—COO—Cyc—methyl
   Alkyl—A—Cyc—COO—Cyc—ethyl
   Alkyl—A—Cyc—COO—Cyc—propyl
   Alkyl—A—Cyc—COO—Cyc—butyl
   Alkyl—A—Cyc—COO—Cyc—pentyl
   Alkyl—A—Cyc—COO—Cyc—hexyl
   Alkyl—A—Cyc—COO—Cyc—heptyl
   Alkyl—A—Cyc—COO—Cyc—octyl
   Alkyl—A—Cyc—COO—Cyc—nonyl
   Alkyl—A—Cyc—COO—Cyc—decyl
XXVII.
   Alkyl—A—Cyc—COO—Phe—CN
   Alkyl—A—Cyc—COO—Phe—methyl
   Alkyl—A—Cyc—COO—Phe—ethyl
   Alkyl—A—Cyc—COO—Phe—propyl
   Alkyl—A—Cyc—COO—Phe—butyl
   Alkyl—A—Cyc—COO—Phe—pentyl
   Alkyl—A—Cyc—COO—Phe—hexyl
   Alkyl—A—Cyc—COO—Phe—heptyl
   Alkyl—A—Cyc—COO—Phe—octyl
   Alkyl—A—Cyc—COO—Phe—nonyl
   Alkyl—A—Cyc—COO—Phe—decyl
XXVIII.
   Alkyl—A—Cyc—COO—Phe'methoxy
   Alkyl—A—Cyc—COO—Phe—ethoxy
   Alkyl—A—Cyc—COO—Phe—propoxy
   Alkyl—A—Cyc—COO—Phe—butoxy
   Alkyl—A—Cyc—COO—Phe—pentoxy
   Alkyl—A—Cyc—COO—Phe—hexoxy
   Alkyl—A—Cyc—COO—Phe—heptoxy
   Alkyl—A—Cyc—COO—Phe—octoxy
   Alkyl—A—Cyc—COO—Phe—nonoxy
   Alkyl—A—Cyc—COO—Phe—decoxy
XXIX.
   Alkyl—A—OCO—Cyc—methyl
   Alkyl—A—OCO—Cyc—ethyl
   Alkyl—A—OCO—Cyc—propyl
   Alkyl—A—OCO—Cyc—butyl
   Alkyl—A—OCO—Cyc—pentyl
   Alkyl—A—OCO—Cyc—hexyl
   Alkyl—A—OCO—Cyc—heptyl
   Alkyl—A—OCO—Cyc—octyl
   Alkyl—A—OCO—Cyc—nonyl
   Alkyl—A—OCO—Cyc—decyl
XXX.
   Alkyl—A—OCO—Phe—methyl
   Alkyl—A—OCO—Phe—ethyl
   Alkyl—A—OCO—Phe—propyl
   Alkyl—A—OCO—Phe—butyl
   Alkyl—A—OCO—Phe—pentyl
   Alkyl—A—OCO—Phe—hexyl
   Alkyl—A—OCO—Phe—heptyl
   Alkyl—A—OCO—Phe—octyl
   Alkyl—A—OCO—Phe—nonyl
   Alkyl—A—OCO—Phe—decyl
XXXI.
   Alkyl—A—OCO—Phe—methoxy
   Alkyl—A—OCO—Phe—ethoxy
   Alkyl—A—OCO—Phe—propoxy
   Alkyl—A—OCO—Phe—butoxy
   Alkyl—A—OCO—Phe—pentoxy
   Alkyl—A—OCO—Phe—hexoxy
   Alkyl—A—OCO—Phe—heptoxy
   Alkyl—A—OCO—Phe—octoxy
   Alkyl—A—OCO—Phe—nonoxy
   Alkyl—A—OCO—Phe—decoxy
XXXII.
   Alkyl—A—OCO—Dio—methyl
   Alkyl—A—OCO—Dio—ethyl
   Alkyl—A—OCO—Dio—propyl
   Alkyl—A—OCO—Dio—butyl
   Alkyl—A—OCO—Dio—pentyl
   Alkyl—A—OCO—Dio—hexyl
   Alkyl—A—OCO'Dio—heptyl
   Alkyl—A—OCO—Dio—octyl
   Alkyl—A—OCO—Dio—nonyl
   Alkyl—A—OCO—Dio—decyl
XXXIII.
   Alkyl—A—CH$_2$CH$_2$—Phe—Phe—CN
   Alkyl—A—CH$_2$CH$_2$—Phe—Phe—methyl
   Alkyl—A—CH$_2$CH$_2$—Phe—Phe—ethyl
   Alkyl—A—CH$_2$CH$_2$—Phe—Phe—propyl
   Alkyl—A—CH$_2$CH$_2$—Phe—Phe—butyl
   Alkyl—A—CH$_2$CH$_2$—Phe—Phe—pentyl
   Alkyl—A—CH$_2$CH$_2$—Phe—Phe—hexyl
   Alkyl—A—CH$_2$CH$_2$—Phe—Phe—heptyl
   Alkyl—A—CH$_2$CH$_2$—Phe—Phe—octyl
   Alkyl—A—CH$_2$CH$_2$—Phe—Phe—nonyl
   Alkyl—A—CH$_2$CH$_2$—Phe—Phe—decyl
XXXIV.
   Alkyl—A—CH$_2$CH$_2$—Phe—(2—F—Phe)—CN
   Alkyl—A—CH$_2$CH$_2$—Phe—(2—F—Phe)—methyl
   Alkyl—A'CH$_2$CH$_2$—Phe—(2—F—Phe)—ethyl
   Alkyl—A—CH$_2$CH$_2$—Phe—(2—F—Phe)—propyl
   Alkyl—A—CH$_2$CH$_2$—Phe—(2—F—Phe)—butyl
   Alkyl—A—CH$_2$CH$_2$—Phe—(2—F—Phe)—pentyl
   Alkyl—A—CH$_2$CH$_2$—Phe—(2—F—Phe)—hexyl
   Alkyl—A—CH$_2$CH$_2$—Phe—(2—F—Phe)—heptyl
   Alkyl—A—CH$_2$CH$_2$—Phe—(2—F—Phe)—octyl
   Alkyl—A—CH$_2$CH$_2$—Phe—(2—F—Phe)—nonyl
   Alkyl—A—CH$_2$CH$_2$—Phe—(2—F—Phe)—decyl
XXXV.
   Alkyl—A—CH$_2$CH$_2$—Phe—(2-F—Phe)—methoxy
   Alkyl—A—CH$_2$CH$_2$—Phe—(2—F—Phe)—ethoxy
   Alkyl—A—CH$_2$CH$_2$—Phe—(2—F—Phe)—propoxy
   Alkyl—A—CH$_2$CH$_2$—Phe—(2-F—Phe)—butoxy
   Alkyl—A—CH$_2$CH$_2$—Phe—(2—F—Phe)—pentoxy
   Alkyl—A—CH$_2$CH$_2$—Phe—(2—F—Phe)—hexoxy
   Alkyl—A—CH$_2$CH$_2$—Phe—(2—F—Phe)—heptoxy
   Alkyl—A—CH$_2$CH$_2$—Phe—(2—F—Phe)—octoxy
   Alkyl—A—CH$_2$CH$_2$—Phe—(2—F—Phe)—nonoxy
   Alkyl—A—CH$_2$CH$_2$—Phe—(2—F—Phe)—decoxy
XXXVI.
   Alkyl—A—CH$_2$O—Phe—Pyr—methyl
   Alkyl—A—CH$_2$O—Phe—Pyr—ethyl
   Alkyl—A—CH$_2$O—Phe—Pyr—propyl
   Alkyl—A—CH$_2$O—Phe—Pyr—butyl
   Alkyl—A—CH$_2$O—Phe—Pyr—pentyl
   Alkyl—A—CH$_2$O—Phe—Pyr—hexyl
   Alkyl—A—CH$_2$O—Phe—Pyr—heptyl
   Alkyl—A—CH$_2$O—Phe—Pyr—octyl Alkyl—A—CH₂O—Phe—Pyr—nonyl
Alkyl—A—CH₂O—Phe—Pyr—decyl
XXXVII.
Alkyl—A—CH₂CH₂—Cyc—CN
Alkyl—A—CH₂CH₂—Cyc—methyl
Alkyl—A—CH₂CH₂—Cyc—ethyl
Alkyl—A—CH₂CH₂—Cyc—propyl
Alkyl—A—CH₂CH₂—Cyc—butyl
Alkyl—A—CH₂CH₂—Cyc—pentyl
Alkyl—A—CH₂CH₂—Cyc—hexyl
Alkyl—A—CH₂CH₂—Cyc—heptyl
Alkyl—A—CH₂CH₂—Cyc—octyl
Alkyl—A—CH₂CH₂—Cyc—nonyl
Alkyl—A—CH₂CH₂—Cyc—decyl
wherein A is 3,1-cyclopentylene, tetrahydrofuran-2,5-diyl or 1,3-dioxolane-2,5-diyl,
wherein
Phe is 1,4-phenylene,
Phe-2-F is 2-fluoro-1,4-phenylene,
Phe-3-F is 3-fluoro-1,4-pentylene,
Cyc is 1,4-cyclohexylene, and
Pyr is Pyrimidine-2,5-diyl.

7. A liquid-crystalline phase of claim 1, wherein in said formula $A^1$, $A^2$ and $A^3$ are Cyp, Cy, Phe, Dio or Pyr, wherein Cyp is 1,3-cyclopentylene in which one or two non-neighboring CH₂-groups may be replaced by O and/or S;
Phe is 1,4-phenylene which is unsubstituted or substituted by one or two F and/or Cl atoms and/or CH₃-groups and/or CN groups;
Cy is 1,4-cyclohexylene; and
Pyr is pyrimidine-2,5-diyl which is unsubstituted or substituted by one or two F and/or Cl atoms and/or CH₃-groups and/or CN groups,
and Dio is 1,3-dioxane-2,5-diyl.

8. A liquid-crystalline phase of claim 1, wherein at least one of $A^1$, $A^2$ and $A^3$ is 1,3-cyclopentylene.

9. A liquid-crystalline phase of claim 1, wherein $Z^1$ and $Z^2$ are single bonds, —CO—O—, —O—CO— or —CH₂CH₂—.

10. A liquid-crystalline phase of claim 1, wherein $R^1$ and $R^2$ are alkyl or alkoxy.

11. A liquid-crystalline phase of claim 1, wherein $R^1$ and $R^2$ are straight chain alkyl or alkoxy.

12. A liquid-crystal display element containing on a liquid-crystalline phase, wherein the phase is one of claim 1.

13. An electro-optical display element containing on a liquid-crystalline dielectric, wherein the dielectric is a phase of claim 1.

14. A phase of claim 1, wherein $R^1$ and $R^2$, in each case independently of one another, are alkyl of 1-15 carbon atoms, or alkyl of 1-15 carbon atoms in which one or more non-adjacent CH₂ groups are replaced by —O—, —O—CO—, —CHhalogen—, —CHCN' and/or —CH=CH—, and one of $R^1$ and $R^2$ can also be F, Cl, CN or —NCS, $Z^1$ and $Z^2$ in each case independently of one another, are —CO—O', —O—CO—, —CH₂CH₂—, —CH₂—O', —OCH₂— or a single bond, and one of $Z^1$ and $Z^2$ can also be —CO—, and $A^1$, $A^2$ and $A^3$ in each case independently of one another, are 1,4-phenylene, 1,4-phenylene in which one or more CH groups are replaced by N, 1,4-cyclohexylene, 1,4-cyclohexylene in which one or two non-adjacent CH₂ groups are replaced by O and/or S, 1,3-cyclopentylene, 1,3-cyclopentylene in which one or two non-adjacent CH₂ groups are replaced by O and/or S or 1,4-bicyclo-(2,2,2)-octylene, each of which can also be substituted by halogen, nitrile and/or alkyl.

15. A phase of claim 1, wherein in $R^1$ and $R^2$, each of said alkyl moieties is of 3-15 C atoms.

* * * * *

UNITED STATES PATENT AND TRADEMARK OFFICE
CERTIFICATE OF CORRECTION

PATENT NO. : 4,873,019

DATED : October 10, 1989

INVENTOR(S) : KRAUSE ET AL

It is certified that error appears in the above-identified patent and that said Letters Patent is hereby corrected as shown below:

Column 21, claim 6, line 24:

reads "Alkyl-Cyc-A'Phe-nonyl"

Should read --Alkyl-Cyc-A-Phe-nonyl --

Column 21, claim 6, line 39:

reads "Cyan-Cyc-Phe-Phe'A-alkyl"

should read --Cyan-Cyc-Phe-Phe-A-alkyl --

Column 23, claim 6, line 38:

reads "Alkyl-A-Cyc-COO-Phe'methoxy"

should read --Alkyl-A-Cyc-COO-Phe-methoxy --

Column 24, claim 6, line 39:

reads "Alkyl-A'$CH_2CH_2$-Phe-(2-F-Phe)-ethyl"

should read -- Alkyl-A-$CH_2CH_2$-Phe-(2-F-Phe)-ethyl --

Signed and Sealed this

Twenty-third Day of October, 1990

*Attest:*

HARRY F. MANBECK, JR.

*Attesting Officer*      *Commissioner of Patents and Trademarks*